United States Patent
Zaman et al.

(10) Patent No.: US 10,125,072 B2
(45) Date of Patent: Nov. 13, 2018

(54) MN/CEO₂ CATALYST FOR DIMETHYL ETHER PRODUCTION VIA OXIDATIVE DEHYDRATION OF METHANOL

(71) Applicant: King Abdulaziz University, Jeddah (SA)

(72) Inventors: Sharif F. Zaman, Jeddah (SA); Hitoshi Inokawa, Jeddah (SA); Muhammad A. Daous, Jeddah (SA); Abdulrahim Al-Zahrani, Jeddah (SA); Lachezar Petrov, Jeddah (SA)

(73) Assignee: King Abdulaziz University, Jeddah (SA)

( * ) Notice: Subject to any disclaimer, the term of this patent is extended or adjusted under 35 U.S.C. 154(b) by 75 days.

(21) Appl. No.: 15/468,624

(22) Filed: Mar. 24, 2017

(65) Prior Publication Data
US 2018/0273456 A1   Sep. 27, 2018

(51) Int. Cl.
*C07C 43/00* (2006.01)
*C07C 41/09* (2006.01)
*B01J 23/34* (2006.01)

(52) U.S. Cl.
CPC .............. *C07C 41/09* (2013.01); *B01J 23/34* (2013.01)

(58) Field of Classification Search
None
See application file for complete search history.

(56) References Cited

U.S. PATENT DOCUMENTS 8,541,630 B2   9/2013   Guo et al.

FOREIGN PATENT DOCUMENTS

| CN | 1836775 A | 9/2006 |
|---|---|---|
| EP | 2 228 359 A1 | 9/2010 |
| WO | 2005/026093 A1 | 3/2005 |

OTHER PUBLICATIONS

Taylor et al. Applied Caralysis A: General 126 (1995) 287-296.*
T. Spassova et al., "Catalytic reduction of NO with decomposed methanol on alumina-supported Mn-Ce catalysts," Journal of Colloid and Interface Science, May 15, 2012, vol. 374, No. 1, pp. 267-277.
Xingang Li et al., "Direct Synthesis of Ethanol from Dimethyl Ether and Syngas over Combined H-Mordenite and Cu/ZnO Catalysts," Aug. 16, 2010.
Weiguo Song et al., "An Oft-Studied Reaction That May Never Have Been: Direct Catalytic Conversion of Methanol or Dimethyl Ether to Hydrocarbons on the Solid Acids HZSM-5 or HSAPO-34," Journal of the American Chemical Society, Feb. 19, 2002, vol. 124, pp. 3844-3845.
Patricia Cheung et al., "Selective Carbonylation of Dimethyl Ether to Methyl Acetate Catalyzed by Acidic Zeolites," Angewandte Chemie, 2006, vol. 45, pp. 1617-1620.
Haichao Liu et al., "Structure and support effects on the selective oxidation of dimethyl ether to formaldehyde catalyzed by $MoO_x$ domains," Journal of Catalysis, 2003, vol. 217, pp. 222-232.
Jian Sun et al., "Catalysis Chemistry of Dimethyl Ether Synthesis," American Chemical Society, 2014, vol. 4, pp. 3346-3356.
Siranush S. Akarmazyan et al., "Methanol dehydration to dimethylether over $Al_2O_3$ catalysts," Applied Catalysis B: Environmental, 2014, vol. 145, pp. 136-148.
Dianhua Liu et al., "Catalytic dehydration of methanol to dimethyl ether over modified $\gamma$-$Al_2O_3$ catalyst," Fuel, 2011, vol. 90, pp. 1738-1742.
Jinhua Fei et al., "Synthesis of dimethyl ether (DME) on modified HY zeolite and modified HY zeolite-supported Cu—Mn—Zn catalysts," Applied Catalysis A: General, 2006, vol. 304, pp. 49-54.
Poul Georg Moses et al., "Methanol to Dimethyl Ether over ZSM-22: A Periodic Density Functional Theory Study," American Chemical Society, Feb. 26, 2013, vol. 3, pp. 735-745.
Qi Yang et al., "Aluminum Fluoride Modified HZSM-5 Zeolite with Superior Performance in Synthesis of Dimethyl Ether from Methanol," Energy & Fuels, 2012, vol. 26, pp. 4475-4480.
F. Yaripour et al., "Catalytic dehydration of methanol to dimethyl ether (DME) over solid-acid catalysts," Catalysis Communications, 2005, vol. 6, pp. 147-152.
R. Ladera et al., "Supported $WO_x$-based catalysts for methanol dehydration to dimethyl ether," Fuel, 2013, vol. 113, pp. 1-9.
Dingfeng Jin et al., "Dimethyl ether synthesis via methanol and syngas over rare earthmetals modified zeolite Y and dual Cu—Mn—Zn catalysts," Fuel, 2007, vol. 86, pp. 2707-2713.

* cited by examiner

*Primary Examiner* — Ana Z Muresan
(74) *Attorney, Agent, or Firm* — Oblon, McClelland, Maier & Neustadt, L.L.P.

(57) ABSTRACT

A method of producing dimethyl ether involving contacting methanol with a catalyst in the presence of oxygen in a reactor to form the dimethyl ether. The catalyst comprises manganese on a cerium oxide catalyst support, wherein a weight ratio of manganese to the cerium oxide catalyst support is in the range of 0.005 to 0.5. Further, a method of manufacturing the catalyst, including mixing cerium oxide ($CeO_2$) with a solution comprising manganese salt and a solvent, evaporating the solvent, followed by drying and calcining to form a catalyst which comprises manganese on a cerium oxide catalyst support, wherein a weight ratio of manganese to the cerium oxide catalyst support is in the range of 0.005 to 0.5.

13 Claims, 6 Drawing Sheets

MN/CEO$_2$ CATALYST FOR DIMETHYL ETHER PRODUCTION VIA OXIDATIVE DEHYDRATION OF METHANOL

BACKGROUND OF THE INVENTION

Technical Field

The present invention relates to catalysts for producing dimethyl ether by oxidative dehydration of methanol.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dimethyl ether (DME) has attracted attention as an additive for diesel fuel, because of its physical and chemical properties. DME has a relatively high cetane number and since a DME molecule does not contain a C—C bond, very small amounts of soot are formed during a combustion process in a combustion engine. DME is a colorless and nontoxic compound that is in a liquid state at room temperature (20-30° C.) and elevated pressure e.g. at least 7 bars. Accordingly, liquefied DME can be stored and transported like other liquid diesel fuels. In the liquid state, DME may be blended with Liquefied Petroleum Gas (LPG). DME can be used not only as a diesel fuel but also as a mother liquor to produce many valuable chemicals. DME can be transformed into olefins, aromatics and other organic chemicals such as methyl acetate, formaldehyde and ethanol. Thus, DME has diverse commercial uses. See W. Song, D. M. Marcus, H. Fu, J. O. Ehresmann, J. F. Haw, An Oft-Studied Reaction That May Never Have Been: Direct Catalytic Conversion of Methanol or Dimethyl Ether to Hydrocarbons on the Solid Acids HZSM-5 or HSAPO-34, Journal of the American Chemical Society, 124 (2002) 3844-3845; P. Cheung, A. Bhan, G. J. Sunley, E. Iglesia, Selective Carbonylation of Dimethyl Ether to Methyl Acetate Catalyzed by Acidic Zeolites, Angewandte Chemie International Edition, 45 (2006) 1617-1620; H. Liu, P. Cheung, E. Iglesia, Structure and support effects on the selective oxidation of dimethyl ether to formaldehyde catalyzed by MoOx domains, Journal of Catalysis, 217 (2003) 222-232; X. Li, X. San, Y. Zhang, T. Ichii, M. Meng, Y. Tan, N. Tsubaki, Direct Synthesis of Ethanol from Dimethyl Ether and Syngas over Combined H-Mordenite and Cu/ZnO Catalysts, ChemSusChem, 3 (2010) 1192-1199, each incorporated herein by reference in their entirety. The size of the global market of DME is estimated to be 3,740.46 kilo tons in 2014, and a compound average growth rate is 15.67% in between 2015 and 2020. See Dimethyl Ether Market by Raw Materials (Coal, Methanol, Natural gas and Bio-based feedstock), by Applications (Aerosol Propellant, LPG Blending, Transportation fuel and Others), and by Region—Trends & forecasts to 2020, in, 2015, incorporated herein by reference in its entirety. DME is mainly synthesized by dehydration of methanol. Generally, acid catalysts (i.e. γ-alumina, zeolites etc.) are used for the dehydration reaction to produce DME. See J. Sun, G. Yang, Y. Yoneyama, N. Tsubaki, Catalysis Chemistry of Dimethyl Ether Synthesis, ACS Catalysis, 4 (2014) 3346-3356, incorporated herein by reference in its entirety.

Reports indicate that acidic catalysts are used for the production of DME from methanol via dehydration. Gamma-alumina (γ-Al$_2$O$_3$) has been reported as the most promising catalyst because of its low cost, high DME selectivity, great thermal and mechanical stability. See S. S. Akarmazyan, P. Panagiotopoulou, A. Kambolis, C. Papadopoulou, D. I. Kondarides, Methanol dehydration to dimethylether over Al2O3 catalysts, Applied Catalysis B: Environmental, 145 (2014) 136-148 and D. Liu, C. Yao, J. Zhang, D. Fang, D. Chen, Catalytic dehydration of methanol to dimethyl ether over modified γ-Al2O3 catalyst, Fuel, 90 (2011) 1738-1742, each incorporated herein by reference in their entirety. The reported performance of γ-Al$_2$O$_3$ is organized in Table 1. Zeolites (such as HZSM-5, HY, HZSM-22 and H-SAPO) have strong acidic sites and also been investigated as a potential catalyst for dehydration of methanol. See J. Fei, Z. Hou, B. Zhu, H. Lou, X. Zheng, Synthesis of dimethyl ether (DME) on modified HY zeolite and modified HY zeolite-supported Cu—Mn—Zn catalysts, Applied Catalysis A: General, 304 (2006) 49-54; D. Jin, B. Zhu, Z. Hou, J. Fei, H. Lou, X. Zheng, Dimethyl ether synthesis via methanol and syngas over rare earth metals modified zeolite Y and dual Cu—Mn—Zn catalysts, Fuel, 86 (2007) 2707-2713; P. G. Moses, J. K. Norskov, Methanol to Dimethyl Ether over ZSM-22: A Periodic Density Functional Theory Study, ACS Catalysis, 3 (2013) 735-745; Q. Yang, M. Kong, Z. Fan, X. Meng, J. Fei, F.-S. Xiao, Aluminum Fluoride Modified HZSM-5 Zeolite with Superior Performance in Synthesis of Dimethyl Ether from Methanol, Energy & Fuels, 26 (2012) 4475-4480, each incorporated herein by reference in its entirety. Unfortunately, in parallel with the main reaction, a formation of considerable amounts of byproducts such as hydrocarbons and coke takes place, resulting in deactivation of the catalyst. In order to improve the activity and stability of the zeolite, it was mechanically mixed with CeO$_2$, but the addition of CeO$_2$ did not show any positive effect. See D. Jin, B. Zhu, Z. Hou, J. Fei, H. Lou, X. Zheng, Dimethyl ether synthesis via methanol and syngas over rare earth metals modified zeolite Y and dual Cu—Mn—Zn catalysts, Fuel, 86 (2007) 2707-2713, incorporated herein by reference in its entirety.

TABLE 1

Catalytic activity and selectivity performance of the existing catalysts

| Catalyst | Temp. (° C.) | SV | Conversion (%) | Selectivity DME (%) | Ref. |
|---|---|---|---|---|---|
| γ-Al$_2$O$_3$ | 150-400 | 2500 (h$^{-1}$) | 90 | 100 | S.S. Akarmazyan, P. Panagiotopoulou, A. Kambolis, C. Papadopoulou, D.I. Kondarides, Methanol dehydration to dimethylether over Al2O3 catalysts, Applied Catalysis B: Environmental, 145 (2014) 136-148. |

TABLE 1-continued

Catalytic activity and selectivity performance of the existing catalysts

| Catalyst | Temp. (°C.) | SV | Conversion (%) | Selectivity DME (%) | Ref. |
|---|---|---|---|---|---|
| $\gamma$-Al$_2$O$_3$ modified with Nb$_2$O$_3$ | 240-340 | 1 (h$^{-1}$) | 87 | No info. | D. Liu, C. Yao, J. Zhang, D. Fang, D. Chen, Catalytic dehydration of methanol to dimethyl ether over modified $\gamma$-Al2O3 catalyst, Fuel, 90 (2011) 1738-1742. |
| $\gamma$-Al$_2$O$_3$ modified with SiO$_2$ | 300 | 15600 (h$^{-1}$) | 86.4 | 100 | F. Yaripour, F. Baghaei, I. Schmidt, J. Perregaard, Catalytic dehydration of methanol to dimethyl ether (DME) over solid-acid catalysts, Catalysis Communications, 6 (2005) 147-152. |
| H-Y, and Fe-, Co-, Ni-, Cr-, Zr-ion exchanged Y zeolite | 245 | 6000 (ml h$^{-1}$ g$_{cat}^{-1}$) | 86 | No info. | J. Fei, Z. Hou, B. Zhu, H. Lou, X. Zheng, Synthesis of dimethyl ether (DME) on modified HY zeolite and modified HY zeolite-supported Cu—Mn—Zn catalysts, Applied Catalysis A: General, 304 (2006) 49-54. |
| H-Y zeolite | 245 | 6000 (ml h$^{-1}$ g$_{cat}^{-1}$) | 87.5 | 92.1 | D. Jin, B. Zhu, Z. Hou, J. Fei, H. Lou, X. Zheng, Dimethyl ether synthesis via methanol and syngas over rare earth metals modified zeolite Y and dual Cu—Mn—Zn catalysts, Fuel, 86 (2007) 2707-2713. |
| CeO$_2$ mixed H-Y zeolite | 245 | 6000 (ml h$^{-1}$ g$_{cat}^{-1}$) | 84.6 | 92.3 | D. Jin, B. Zhu, Z. Hou, J. Fei, H. Lou, X. Zheng, Dimethyl ether synthesis via methanol and syngas over rare earth metals modified zeolite Y and dual Cu—Mn—Zn catalysts, Fuel, 86 (2007) 2707-2713. |
| TiO$_2$ | 300 | 6.9 (mmol$_{CH3OH}$ h$^{-1}$ g$_{cat}^{-1}$) | 4 | 84 | R. Ladera, E. Finocchio, S. Rojas, G. Busca, J.L.G. Fierro, M. Ojeda, Supported WOx-based catalysts for methanol dehydration to dimethyl ether, Fuel, 113 (2013) 1-9. |
| WOx modified TiO$_2$ | 300 | 6.9 (mmol$_{CH3OH}$ h$^{-1}$ g$_{cat}^{-1}$) | 15 | 82 | R. Ladera, E. Finocchio, S. Rojas, G. Busca, J.L.G. Fierro, M. Ojeda, Supported WOx-based catalysts for methanol dehydration to dimethyl ether, Fuel, 113 (2013) 1-9. |

In view of the forgoing, a first objective of the present invention is to provide a method of manufacturing of a catalyst comprising manganese (Mn) supported on cerium oxide, and a second objective is to provide a method of producing dimethyl ether by oxidative dehydration of methanol.

BRIEF SUMMARY OF THE INVENTION

According to a first aspect, the present disclosure relates to a method for producing dimethyl ether that involves contacting methanol with a Mn/CeO$_2$ catalyst in a reactor to form the dimethyl ether. The catalyst consists of manganese supported on cerium oxide, wherein the manganese-cerium oxide catalyst has a weight percent ratio of manganese relative to cerium oxide of 0.5% to 50%.

In one embodiment, the manganese-cerium oxide catalyst has a grain size of 0.05 mm to 0.5 mm.

In one embodiment, a temperature of the reactor is in the range of 275° C. to 450° C.

In one embodiment, a selectivity percentage for dimethyl ether from the conversion of methanol is in the range of 20-90 mol %.

In one embodiment, the catalyst is contacted with methanol in an oxygen/methanol mixture having a volume to volume ratio in the range of 0.1 to 1.0.

In one embodiment, a selectivity percentage for dimethyl ether from the conversion of methanol is in the range of 20-90 mol %.

In one embodiment, a percentage yield of dimethyl ether, relative to a mol % of the methanol converted, is 10 to 40% over a reaction time of 30 hours to 90 hours.

In one embodiment, the prepared Mn/CeO$_2$ catalyst has surface area of 7 m$^2$/g-12 m$^2$/g measured by Brunauer-Emmett-Teller (BET) method.

In one embodiment, the catalyst consists of a manganese-cerium oxide in a weight percent ratio of manganese relative to cerium oxide of 0.5% to 50%.

According to a second aspect, the present disclosure relates to a method of catalyst preparation. It includes mixing cerium oxide (CeO$_2$) with a solution comprising manganese salt and a solvent, evaporating the solvent from the sludge to obtain solid residue of Mn/CeO$_2$, in form of a powder, drying at 110° C., calcining the solid residue at 90° C. to 500° C. for 5 h, sieving, granulating, and tableting.

In one embodiment, the solvent is water, ethanol, methanol, acetonitrile, or a combination thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

According to a first aspect, the present disclosure relates to a method for producing dimethyl ether involving contacting methanol with a catalyst in a reactor to form the dimethyl ether (DME). The catalyst comprises manganese on a cerium oxide catalyst support. In some embodiments, the catalyst may include manganese oxide, manganese, or both and cerium oxide.

Figure 1:
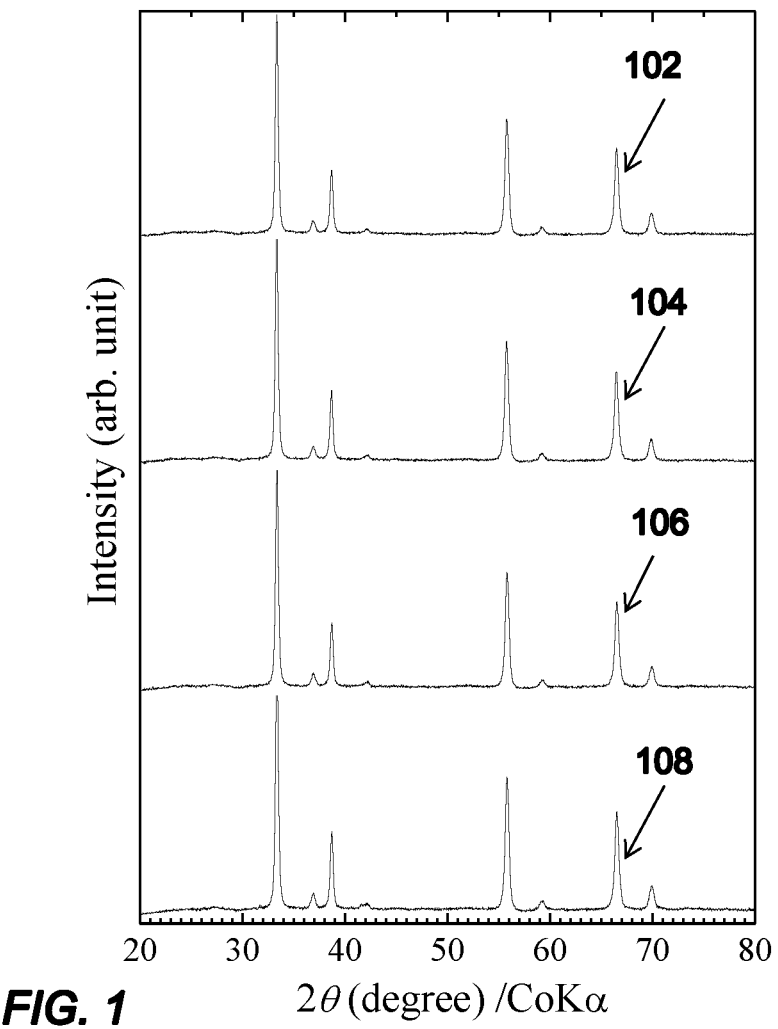
FIG. 1 shows XRD patterns of a CeO$_2$ catalyst, a 1% Mn/CeO$_2$ catalyst, a 3% Mn/CeO$_2$ catalyst, and a 5% Mn/CeO$_2$ catalyst.

Referring now to FIG. 1, in some embodiments, the catalyst includes manganese and the cerium oxide catalyst support, wherein a weight ratio of manganese to the catalyst support is in the range of 0.005 to 0.5, preferably 0.01 to 0.3, preferably 0.01 to 0.1, preferably 0.01 to 0.05, preferably 0.02 to 0.05. FIG. 1 depicts an X-Ray diffraction pattern for an exemplary $CeO_2$ catalyst (FIG. 1—102), an exemplary 1 wt % $Mn/CeO_2$ catalyst (FIG. 1—104), an exemplary 3 wt % $Mn/CeO_2$ catalyst (FIG. 1—106), and an exemplary 5 wt % $Mn/CeO_2$ catalyst (FIG. 1—108).

The catalyst of manganese on a cerium oxide catalyst support may also be denoted as "$Mn/CeO_2$" in this disclosure.

The term "catalyst support" refers to a solid substrate, wherein manganese particles are deposited. The catalyst support may preferably a porous solid that provides a higher surface area for contacting methanol, preferably in the presence of oxygen. Accordingly, in a preferred embodiment, the $Mn/CeO_2$ catalyst has a Brunauer-Emmett-Teller (BET) surface area in the range of 5 $m^2/g$ to 15 $m^2/g$, preferably 6 $m^2/g$ to 14 $m^2/g$, preferably 7 $m^2/g$ to 13 $m^2/g$, preferably 7 $m^2/g$ to 12 $m^2/g$.

The grain size of the $Mn/CeO_2$ catalyst might affect the rate and the selectivity of the oxidative dehydration reactions of methanol, due to the diffusion limitations of methanol or reaction products. Therefore, in some embodiments, the $Mn/CeO_2$ catalyst are granulated and sieved to form catalyst grains with a grain size in the range of 0.05 mm to 0.5 mm, preferably 0.75 mm to 0.4 mm, preferably 0.1 mm to 0.3 mm, preferably 0.2 mm to 0.25 mm.

In the oxidative dehydration of methanol to DME, side products may also be formed. In some embodiments, the side product may be hydrogen, carbon monoxide, carbon dioxide, formaldehyde, or a combination thereof. The formation of the side products is not an objective of the present disclosed catalyst or the method.

In a preferred embodiment, a selectivity of dimethyl ether from a conversion of 50 to 100 mol %, preferably 60 to 95 mol %, preferably 70 to 90 mol % methanol is in the range of 20 to 100%, preferably 30 to 95%, preferably 40 to 90%, preferably 50 to 85%, preferably 60 to 85%, preferably 65 to 80%. The term "selectivity" as used herein refers to a percentile of dimethyl ether produced in moles per moles of methanol consumed. Furthermore, the term "conversion of methanol" refers to a ratio (in percentile) of moles of methanol that is converted in a reactor (i.e. an amount (in mole) of methanol that enters a reactor subtracted by an amount (in mole) of methanol that exits the reactor), relative to the moles of methanol that enters the reactor. The calculations are further described in the Examples herein.

Figure 2:
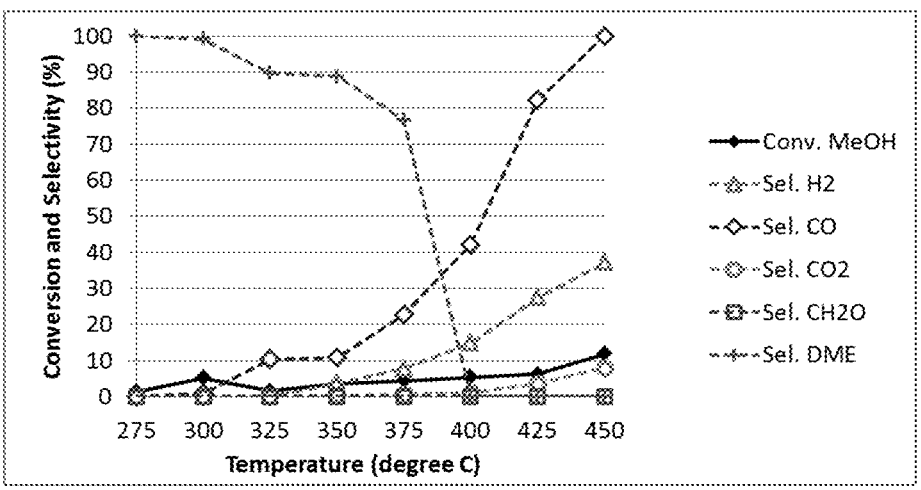
FIG. 2 is a graph depicting a methanol conversion and selectivity percentiles with respect to hydrogen, carbon monoxide, carbon dioxide, formaldehyde, and dimethyl ether, for reactions in the presence of the 1% $Mn/CeO_2$ catalyst, in the absence of an $O_2$ flow.

FIG. 2 represents a diagram of exemplary data of methanol contacting the $Mn/CeO_2$ catalyst in the absence of an oxygen flow. The results depict a low conversion less than or equal to 20 mol %, preferably less than or equal to 10 mol %. A slight increase in the methanol conversion rate at elevated temperatures (i.e. above 350° C., preferably above 400° C.) is observed.

Figure 3:
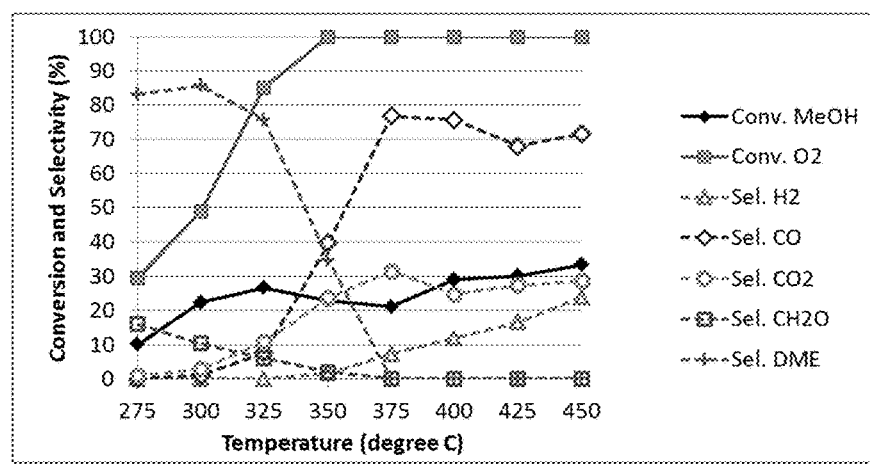
FIG. 3 is a graph depicting a methanol conversion and selectivity percentiles with respect to hydrogen, carbon monoxide, carbon dioxide, formaldehyde, and dimethyl ether, for reactions in the presence of the 1% $Mn/CeO_2$ catalyst, wherein a molar ratio of $O_2$ to methanol is 0.2.
Figure 4:
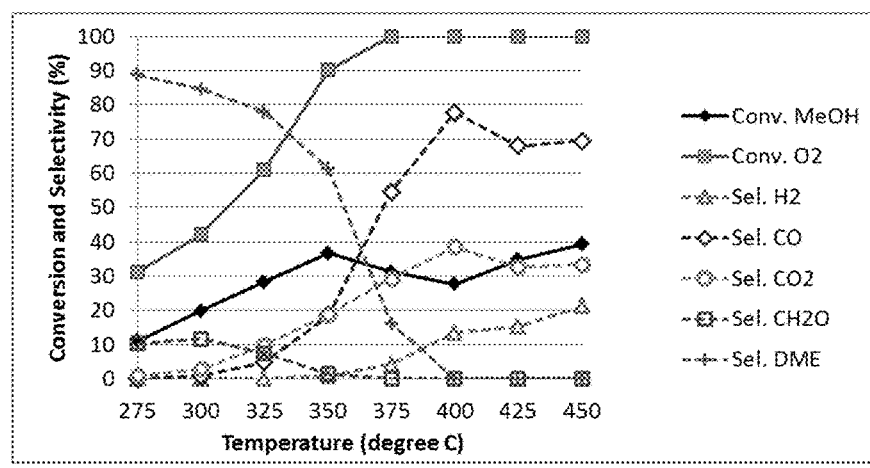
FIG. 4 is a graph depicting a methanol conversion and selectivity percentiles with respect to hydrogen, carbon monoxide, carbon dioxide, formaldehyde, and dimethyl ether, for reactions in the presence of the 1% $Mn/CeO_2$ catalyst, wherein a molar ratio of $O_2$ to methanol is 0.2.
Figure 5:
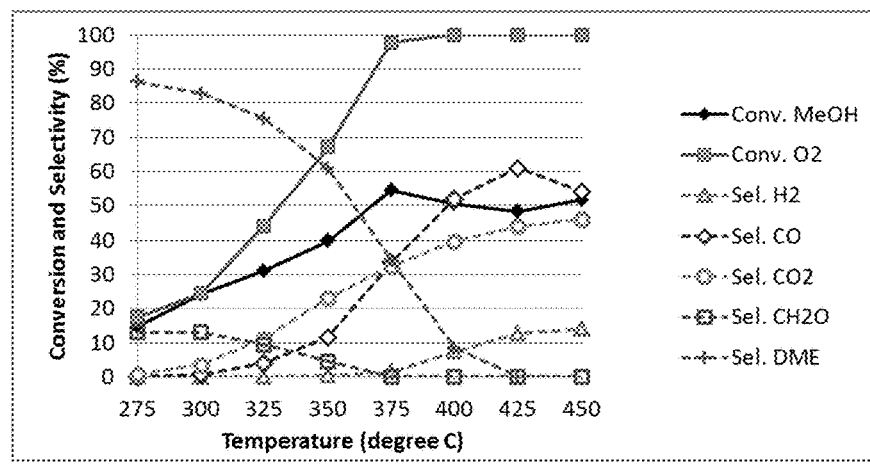
FIG. 5 is a graph depicting a methanol conversion and selectivity percentiles with respect to hydrogen, carbon monoxide, carbon dioxide, formaldehyde, and dimethyl ether, for reactions in the presence of the 1% $Mn/CeO_2$ catalyst, wherein a molar ratio of $O_2$ to methanol is 0.5.

An implementation of the presently disclosed method increases the conversion of methanol to dimethyl ether by contacting the catalyst with a mixture of methanol and oxygen. The mixture of methanol and oxygen has a molar ratio of oxygen to methanol in the range of 0.1:1 to 1:1, preferably 0.1:1 to 0.6:1, preferably 0.2:1 to 0.6:1, preferably 0.2:1 to 0.5:1. FIG. 3, FIG. 4, and FIG. 5 depict data from three exemplary catalyst reaction tests of the catalyst having a 1% $Mn/CeO_2$, wherein a molar ratio of oxygen to methanol is 0.2:1, 0.3:1, and 0.5:1, respectively. In some embodiments, as shown in FIGS. 3, 4 and 5, 10 mol % to 50 mol %, preferably 10 mol % to 40 mol %, preferably 10 mol % to 30 mol % of the methanol is converted to dimethyl ether or at least one side product (hydrogen, carbon monoxide, carbon dioxide, and formaldehyde). Selectivity of dimethyl ether from the conversion of methanol may depend on the reaction temperature. Therefore, in all embodiments, a temperature of the reactor is in the range of 275° C. to 450° C., preferably 275° C. to 400° C., preferably 275° C. to 350° C. Accordingly, the selectivity of dimethyl ether is in the range of 75 mol %-85 mol % or 80 mol % to 90 mol % in the temperature range between in the range of 275° C. to 450° C., preferably 275° C. to 400° C., preferably 275° C. to 350° C. in the presence of an $O_2$ flow. The side products formed may be in the range of 0 to 20%, preferably 0 to 15%, more preferably 0 to 10% of the converted methanol in the above reaction temperature ranges.

In one embodiment, 20 mol % to 100 mol %, preferably 30 mol % to 100 mol %, more preferably 40 mol % to 100 mol % of the oxygen is converted to dimethyl ether or at least one of carbon monoxide, carbon dioxide, formaldehyde, and/or water.

In one embodiment, the catalyst remains stable during oxidative dehydration reactions in the reaction temperature of 275° C. to 450° C., preferably 275° C. to 400° C., preferably 275° C. to 375° C., preferably 300° C. to 375° C., for at least 50 hours, preferably at least 60 hours, preferably at least 65 hours, preferably at least 70 hours, preferably at least 75 hours, preferably at least 80 hours, preferably at least 85 hours, preferably at least 90 hours, preferably at least 95 hours, preferably at least 100 hours. The catalyst's stability may be measured by a percent of deactivation. The term "deactivation" as used herein refers to a loss of catalytic activity (as a measure of reaction rate decrease with time), which classifies as deactivation by type (chemical, thermal, and mechanical) and by mechanism (poisoning, fouling, thermal degradation, vapor formation, vapor-solid and solid-solid reactions, and attrition/crushing). In one embodiment, a deactivation of the catalyst is used to measure a stability of the catalyst during the oxidative dehydration reactions.

Figure 10:
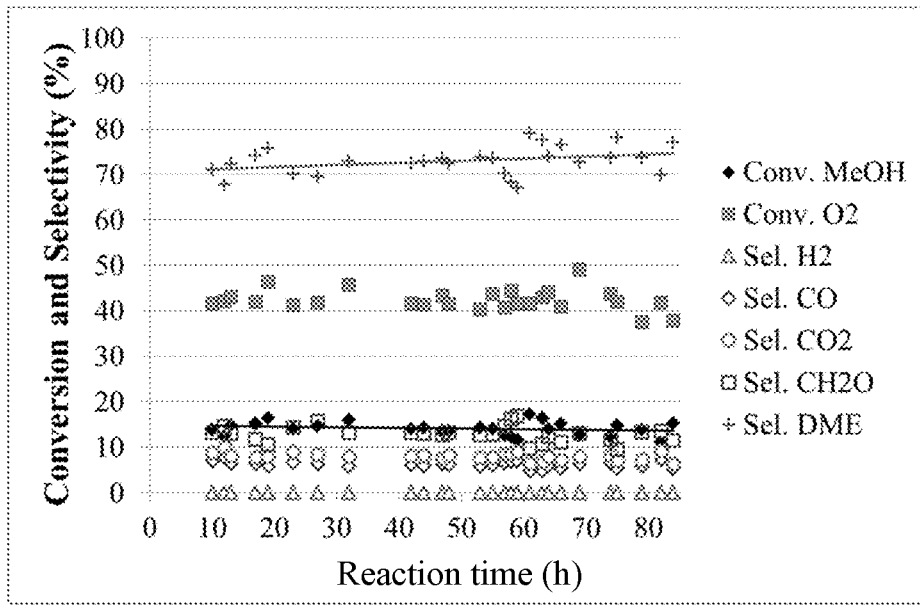
FIG. 10 is a graph depicting data of a stability test of the 1% $Mn/CeO_2$ catalyst.
Figure 11:
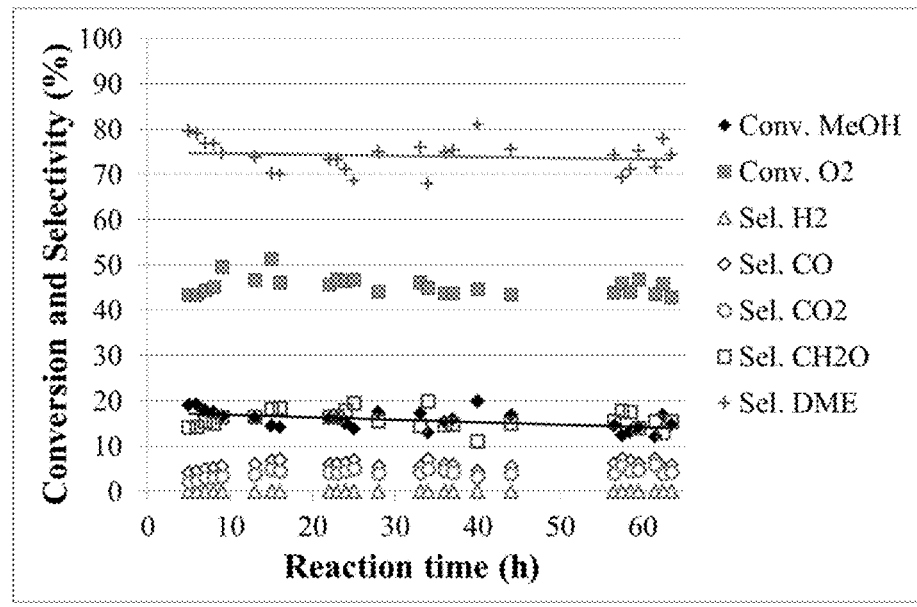
FIG. 11 is a graph depicting data of a stability test of the 3% $Mn/CeO_2$ catalyst.

Referring now to FIG. 10 and FIG. 11, in one embodiment, no decrease in methanol conversion and/or DME selectivity is detected in oxidative dehydration reactions over a period of at least 60 hours, preferably at least 65 hours, preferably at least 70 hours, preferably at least 75 hours, preferably at least 80 hours, preferably at least 85 hours, preferably at least 90 hours, preferably at least 95 hours, preferably at least 100 hours, which indicates that the stability of the catalyst in the reaction conditions, without any catalyst deactivation.

Further in some embodiments, the oxygen and methanol flow rate may be between 0.1 g/h to 0.7 g/h, preferably 0.2 g/h to 0.6 g/h, preferably 0.3 g/h to 0.5 g/h. In some embodiments, methanol or the mixture of methanol and oxygen is mixed with helium with a volumetric ratio of 1:1 to 1:9, preferably 1:2 to 1:6, preferably 1:3 to 1:4. In some embodiments, the methanol/helium or oxygen/methanol/helium gas mixture should be preheated prior to flowing into the reactor at a temperature of 125° C. to 200° C., preferably 130° C. to 170° C., preferably 140° C. to 160° C. In some implementations, the oxygen/methanol/helium flow rate is in the range of 20 mL/min to 75 mL/min, preferably 30 mL/min to 60 mL/min, preferably 40 mL/min to 50 mL/min. In some embodiments, a gas hourly space velocity (GHSV) of the reactor is 10,000 $cm^3\ h^{-1}\ g_{cat}^{-1}$ to 50,000 $cm^3\ h^{-1}\ g_{cat}^{-1}$, preferably 20,000 $cm^3\ h^{-1}\ g_{cat}^{-1}$ to 40,000 $cm^3\ h^{-1}$ $g_{cat}^{-1}$. Gas hourly space velocity relates the flow rate of the mixed gas and the weight of the catalyst, and GHSV is measured at standard temperature and pressure. In some embodiments, the catalyst bed was preheated to a temperature from 200° C. to 300° C., preferably 225° C. to 275° C., preferably 240° C. to 250° C. The preheated catalyst bed may be ramped to a reaction temperature simultaneously with the reactor temperature at a ramping rate of 1° C./min to 10° C./min, preferably 3° C./min to 8° C./min, preferably 5° C./min to 6° C./min. In some embodiments, the pressure of the reactor is 0.5 atm to 1.5 atm, preferably 0.7 atm to 1.25 atm, more preferably 0.8 atm to 1.0 atm.

The reactor may include, but is not limited to a fixed bed flow reactor, a moving bed reactor, or a fluidized bed reactor.

According to a second aspect, the present disclosure relates to a method of manufacturing the $Mn/CeO_2$ catalyst including mixing cerium oxide ($CeO_2$) with a solution comprising a manganese salt and a solvent, evaporating the solvent to form a solid that includes manganese on a cerium oxide catalyst support. The manganese salt may include but is not limited to manganese bromide, manganese chloride, manganese carbonate, manganese fluoride, manganese iodide, manganese sulfate, and/or manganese nitrate.

The term "mixing" as used herein preferably refers to a process that includes mechanical blending or agitation in a vessel by paddles, jets, or baffles. The mixing may occur sequentially or simultaneously. For example the manganese salt may first be dissolved or dispersed in solution, then followed by cerium oxide, or both manganese salt and cerium oxide may be combined in the solution simultaneously mixed. In some implementations, the solvent in which the manganese salt and/or the cerium oxide is prepared by dispersion or dissolution may be water, ethanol, methanol, acetonitrile, or a combination thereof. In some implementations, the solvent is at least 40% water, at least 30% water, at least 20% water, at least 10% water, or at least 1% water. In a preferred embodiment, the solvent is water and the manganese salt is manganese chloride tetra hydrate (i.e. $MnCl_2.4H_2O$). In addition, evaporating may be accomplished by a vacuum evaporation, preferably a rotary evaporation.

The method further involves drying the solid at a temperature of 90° C. to 120° C., preferably around 100° C. for 2 hours to 5 hours, preferably about 3 hours. Besides, the method involves calcining the solid at a temperature of 450° C. to 550° C., preferably around 500° C. for 3 hours to 7 hours, preferably about 4 to 6 hours, more preferably about 5 hours to form the catalyst.

In a preferred embodiment, the method further involves granulating the solid to form catalyst grains in the size range of 0.05 mm and 0.5 mm, preferably 0.06 to 0.3 mm, preferably 0.07 to 0.2 mm, preferably 0.08 to 0.1 mm.

In another preferred embodiment, the grains may further be sieved to collect catalyst grains preferably with uniform shape and size. The sieving may include high frequency vibrating equipment, which drives a screen cloth to vibrate allowing material to be filtered that is smaller than a pore size of the screen; gyratory equipment, which gyrates in a circular motion at a near level plane at low angles to cause a material to shift back and forth and smaller material falls out of the box more easily than heavier material; or a trommel screens, which is a horizontal rotating drum with screen panels around the diameter of the drum through which material may be removed or captured based on size.

The examples below are intended to further illustrate the method of producing dimethyl ether and the method of manufacturing the catalyst and are not intended to limit the scope of the claims.

Example 1

The dehydration of methanol to DME over γ-$Al_2O_3$ and zeolite catalysts is carried out in the absence of oxygen whereas the present invention describes a method to produce DME by oxidative dehydration of methanol over a catalyst composed of manganese supported on cerium oxide (Mn/$CeO_2$). The presently disclosed method employing the Mn/$CeO_2$ catalyst requires minimal oxygen presence in the reaction mixture in order to produce DME from methanol with a high selectivity.

The presently disclosed catalyst, which comprises manganese supported on low surface area $CeO_2$ demonstrates a high catalytic activity and selectivity in the reaction of oxidative dehydration of methanol to DME. The interaction between Mn and $CeO_2$ results in a change of the catalytic properties of the $CeO_2$ as disclosed in data herein. Synergism was observed between deposited Mn and $CeO_2$, which causes an increase in the catalyst efficiency towards producing the dimethyl ether. The result of this synergism was unexpected catalytic properties in the catalyst. Further, by combining a small amount of oxygen to the methanol feed stream, in the presence of Mn/$CeO_2$ catalyst, methanol was transformed to DME with high selectivity relative to side products. The proposed catalyst composition for oxidative dehydration of methanol is different from the conventional catalysts and process for DME production.

Example 2—Preparation of Mn/$CeO_2$ Catalyst

Manganese oxide was added to $CeO_2$ (Acros, Belgium, 99.9%) by incipient wetness impregnation method. To prepare 5 g of 1 wt % Mn supported on $CeO_2$ catalyst, 0.1876 g of Manganese Chloride Tetra Hydrate ($MnCl_2 \cdot 4H_2O$, Techno Pharmchem HARYANA, India, 97%) was dissolved in 10 ml of deionized water at room temperature, resulting in a transparent solution. 5 g of $CeO_2$ was then added to the $MnCl_2$ aqueous solution. Water was then evaporated by using a rotary evaporator having the operating condition at 40° C. and 40-60 mbar. After completing the evaporation, the resulting powder was collected and dried in an oven at 100° C. for 3 h. The powder was then calcined in static air at 500° C. for 5 h. The desired temperature was attained by increasing the oven temperature from 25° C. to 500° C. having a ramping rate of 5° C. $min^{-1}$.

The obtained powder material was tableted, and the tablets were grounded. A fraction of the grounded material with grain size between 0.08 and 0.1 mm was selected and used for catalytic activity and selectivity measurements.

3 wt % and 5 wt % Mn supported on $CeO_2$ catalysts were also prepared by the same procedure as 1 wt % Mn/$CeO_2$ catalyst.

All catalysts are characterized as follows. Crystal structure of the prepared catalysts was characterized by X-ray diffraction. FIG. 1 shows XRD patterns of 1% Mn/$CeO_2$, 3% Mn/$CeO_2$, 5% Mn/$CeO_2$ and pure $CeO_2$ support.

Specific surface area of the catalysts was measured by using $N_2$ adsorption isotherms and Brunauer-Emmett-Teller (BET) analysis. Before the nitrogen adsorption, all the catalysts were degassed at 200° C. for 2 h under vacuum condition in order to remove adsorbates on the catalysts. The values of the surface area are shown in Table 2.

TABLE 2

BET surface area of the catalysts

| Sample | $CeO_2$ support | 1% Mn/$CeO_2$ | 3% Mn/$CeO_2$ | 5% Mn/$CeO_2$ |
|---|---|---|---|---|
| Surface area ($m^2$/g) | 10.0 | 9.6 | 8.6 | 8.0 |

Composition of the catalysts was analyzed by X-ray Fluorescence (XRF) as shown in Table 3. The nominal values (wt %) of Mn content are very close to the desired value of the preparation condition.

TABLE 3

Composition of the catalysts (wt %)

| | 1% Mn/$CeO_2$ | 3% Mn/$CeO_2$ | 5% Mn/$CeO_2$ |
|---|---|---|---|
| Ce | 99.06 | 96.39 | 94.50 |
| Mn | 0.94 | 3.60 | 5.50 |

Example 3—Oxidative Dehydration of Methanol Over 1% Mn/$CeO_2$ Catalysts with Different $O_2$/MeOH Ratios The process of the oxidative dehydration of methanol was carried out by using (PID Eng & Tech, System, Spain) with a fixed bed quartz reactor at atmospheric pressure in the temperature interval between 275 and 450° C. The reactor was charged with 0.1 g of catalyst with grain sizes between 0.08 to 0.1 mm. The catalyst bed was supported on the bed of quartz wool. The internal diameter of the quartz reactor was 4 mm, and the height of the catalyst bed was 7-8 mm. A K-type thermocouple was placed at the center of the catalyst bed to measure the reaction temperature.

Liquid methanol flow was controlled by Bronkhorst High-Teck B.V. CEM system at 0.45 g $h^{-1}$. Oxygen ($O_2$) flow was controlled at $O_2$/MeOH ratio of 0.2, 0.3, and 0.5 (mol/mol) by a mass flow controller (Bronkhorst High-Teck B.V.).

The required methanol and oxygen flow were mixed with helium in a mixing chamber heated at 150° C. The total flow of oxygen, methanol and inert He was 50 ml/min, and gas hourly space velocity (GHSV) was 30,000 $cm^3$ $h^{-1}$ $g_{cat}^{-1}$.

Catalyst bed was preheated to 250° C. prior to introduce the reactants to the reactor. The reactor temperature was then increased to 275° C. at a ramping rate of 5° C./min. For each desired experimental condition, temperature (in between 275-450° C.) was held for 3 h to reach steady state prior to analyze the reaction products. The reactants and products were analyzed with an on-line gas chromatograph (HP, G1540A) equipped with TCD detectors. Molecular sieve 13X was used to separate $O_2$ and CO, and Porapak QS was used to separate $H_2$, $CO_2$, $H_2O$, $CH_2O$ (Formaldehyde), $CH_3OH$ and $CH_3OCH_3$ (Dimethyl ether).

Conversion (%) of reactants and selectivity of products were calculated as follows in equations (1)-(7).

$$CH_3OH \text{ conversion}(\%) = \frac{\text{mol. of } CH_3OH_{in} - \text{mol. of } CH_3OH_{out}}{\text{mol. of } CH_3OH_{in}} \times 100 \quad (1)$$

$$O_2 \text{ conversion}(\%) = \frac{\text{mol. of } O_{2in} - \text{mol. of } O_{2out}}{\text{mol. of } O_{2in}} \times 100 \quad (2)$$

-continued $$CH_2O \text{ selectivity } (\%) = \frac{\text{mol. of } CH_2O}{\text{mol. of } CH_3OH_{consumed}} \times 100 \quad (3)$$

$$CO \text{ selectivity } (\%) = \frac{\text{mol. of } CO}{\text{mol. of } CH_3OH_{consumed}} \times 100 \quad (4)$$

$$CO_2 \text{ selectivity } (\%) = \frac{\text{mol. of } CO_2}{\text{mol. of } CH_3OH_{consumed} \times 100} \quad (5)$$

$$DME(CH_3OCH_3) \text{ selectivity } (\%) = \frac{2 \text{ (mol. of } CH_3OCH_3)}{\text{mol. of } CH_3OH_{consumed}} \times 100 \quad (6)$$

$$DME \text{ yield } (\%) = CH_3OH \text{ conversion} \times DME \text{ selectivity}/100 \quad (7)$$

FIG. 2, FIG. 3, FIG. 4 and FIG. 5 show MeOH conversion and selectivity obtained on 1% $Mn/CeO_2$ at $O_2/MeOH$ ratio of 0, 0.2, 0.3 and 0.5, respectively. DME yields at each $O_2/MeOH$ ratio were compared as shown in FIG. 6.

Figure 6:
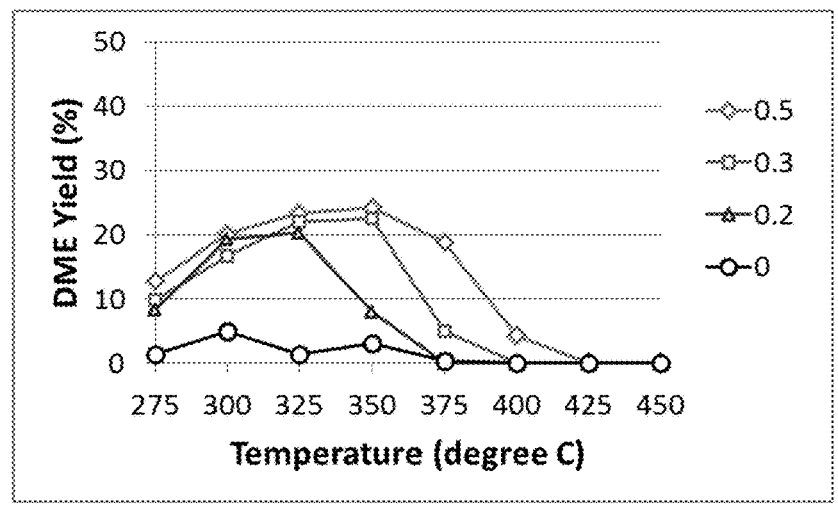
FIG. 6 is a graph depicting a DME yield vs. temperature in the presence of the 1% $Mn/CeO_2$ catalyst, wherein a molar ratio of $O_2$ to methanol is 0, 0.2, 0.3, and 0.5.

The 1% $Mn/CeO_2$ catalyst showed quite small activity at the condition without $O_2$ flow as shown in FIG. 2 and FIG. 6. Conversion measurements below 5% were a result of error in methanol flow rate. At the temperature range between 275° C. and 375° C., a small amount of DME was generated. When $O_2$ was supplied with methanol at $O_2/MeOH$ ratio of 0.2, 0.3 and 0.5, a considerable amount of methanol was reacted and DME was obtained as main product at a temperature range between 275 and 325° C. DME yield was significantly increased with increase of the $O_2$ flow as shown in FIG. 6. These results suggest that DME production over $Mn/CeO_2$ catalyst needs oxygen and follows a different mechanism compared to the dehydration mechanism on $\gamma$-$Al_2O_3$ and on zeolites.

300° C. is an advantageous temperature because conversion at 300° C. is higher than that of 275° C. and DME selectivity at 300° C. is higher than that of at 325° C. Higher $O_2/MeOH$ ratio brought higher selectivity for $CO_2$, resulting in relatively lower DME selectivity. Therefore, it was concluded that the reaction temperature at 300° C. and the $O_2/MeOH$ ratio at 0.2 for oxidative dehydration of methanol to DME, provided a usable level of DME yield.

Figure 7:
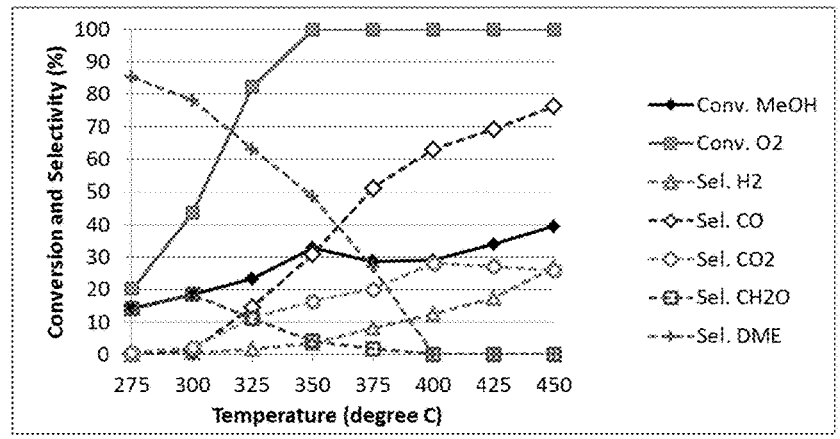
FIG. 7 is a graph depicting a methanol conversion and selectivity percentiles with respect to hydrogen, carbon monoxide, carbon dioxide, formaldehyde, and dimethyl ether, for reactions in the presence of the 3% $Mn/CeO_2$ catalyst, wherein a molar ratio of $O_2$ to methanol is 0.5.
Figure 8:
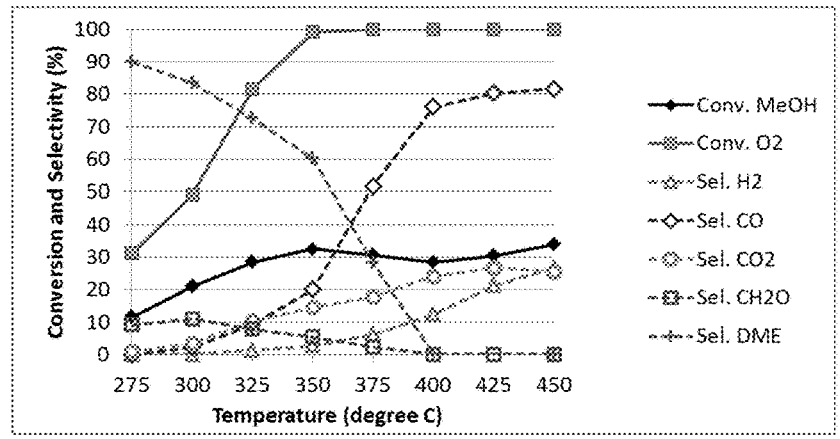
FIG. 8 is a graph depicting a methanol conversion and selectivity percentiles with respect to hydrogen, carbon monoxide, carbon dioxide, formaldehyde, and dimethyl ether, for reactions in the presence of the 5% $Mn/CeO_2$ catalyst, wherein a molar ratio of $O_2$ to methanol is 0.5.
Figure 9:
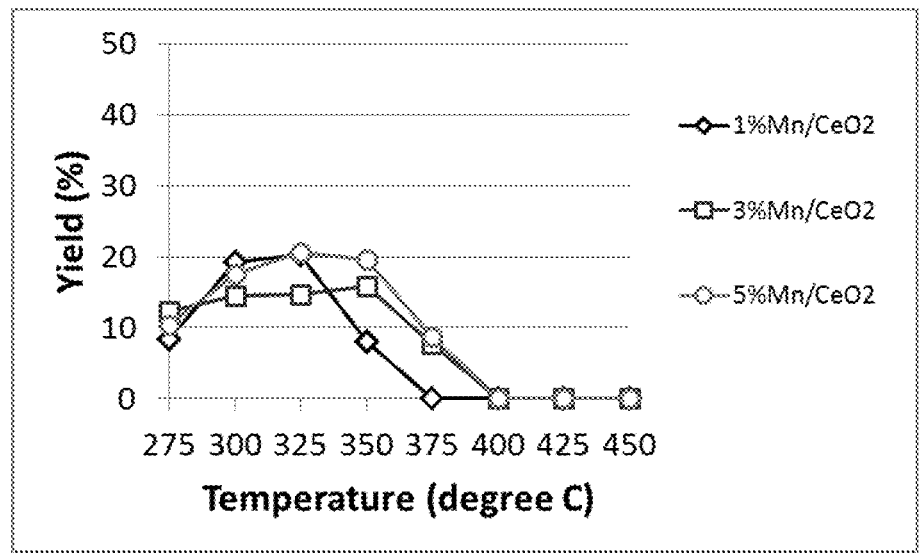
FIG. 9 is a graph depicting a DME yield vs. temperature in the presence of the 1% $Mn/CeO_2$, the 3% $Mn/CeO_2$, and the 5% $Mn/CeO_2$ catalysts.

Example 4—Oxidative Dehydration of Methanol Over $Mn/CeO_2$ Catalysts with Different Mn Contents Activity of 3% $Mn/CeO_2$ and 5% $Mn/CeO_2$ was tested at $O_2/Me$ ratio of 0.2, according to the same procedure as above in the preparation of $Mn/CeO_2$ catalyst, as shown in FIG. 7 and FIG. 8. DME yields obtained over $Mn/CeO_2$ catalysts with different Mn contents were compared as shown in FIG. 9. The increase of Mn content increases DME selectivity at middle temperature range (between 350 and 375° C.). However, at lower temperature such as 275 and 300° C., Mn content hardly influenced the activity and selectivity.

Example 5—Stability Test of 1% and 3% $Mn/CeO_2$ Catalysts at $O_2/MeOH$ Ratio of 0.2

Methanol oxidative dehydration reaction over 1% and 3% $Mn/CeO_2$ was isothermally performed at 300° C. and $O_2/MeOH$ ratio of 0.2 in order to examine the stability of the catalysts. As a result, both 1% $Mn/CeO_2$ and 3% $Mn/CeO_2$ catalysts didn't show any significant deactivation or any decrease in DME selectivity for a time period of 80 hours.

Example 6—Oxidative Dehydration of Methanol Over Manganese Oxide

Figure 14:
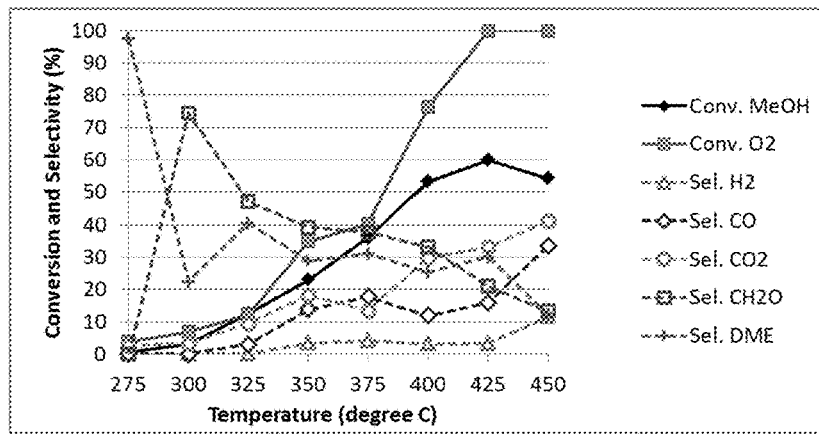
FIG. 14 is a graph depicting methanol and oxygen conversions and selectivity percentiles with respect to hydrogen, carbon monoxide, carbon dioxide, formaldehyde, and dimethyl ether, for reactions in the presence of a manganese oxide catalyst (i.e. MnOx).
Figure 15:
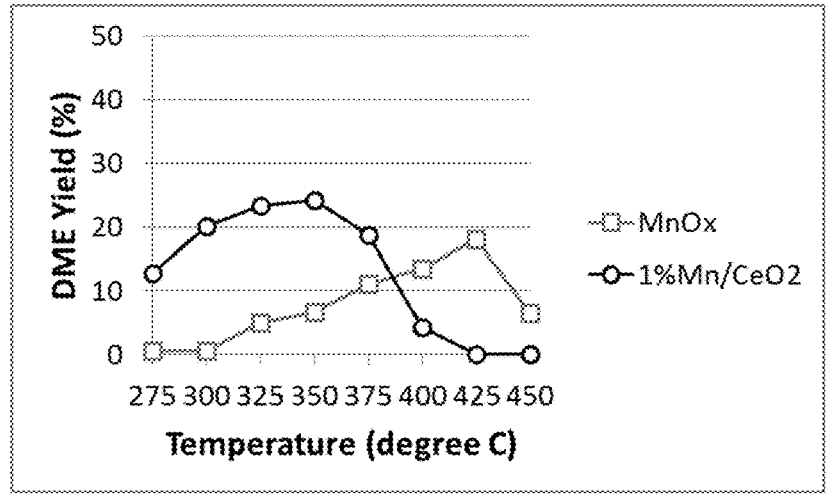
FIG. 15 is a graph depicting a DME yield vs. temperature in the presence of the manganese oxide catalyst and the 1% $Mn/CeO_2$ catalyst.

Manganese oxide (MnOx) was synthesized by calcination of Manganese chloride ($MnCl_2.4H_2O$, Techno Pharmchem HARYANA, 97%) at 500° C. for 5 h according to the same calcination condition to prepare $Mn/CeO_2$ catalysts. The activity of 100 mg of the synthesized MnOx was examined at $O_2/MeOH$ ratio of 0.5 according to the same procedure as $Mn/CeO_2$ catalysts. As a result, MnOx showed much lower activity and DME yield at 300° C. than those of $Mn/CeO_2$ catalysts as shown in FIG. 14 and FIG. 15. In addition, DME selectivity is also lower than $Mn/CeO_2$ catalyst because of increased amount of formaldehyde production.

Example 7

The analysis of the composition of the reaction mixture at the reactor output were done by gas chromatographic method by using the following chromatographic columns of a molecular sieve, Porapak®, Tenax®, hayeSep®, and Chromosorb.

FIG. 6 shows a comparison of data derived from FIG. 3, FIG. 4, and FIG. 5. The highest selectivity for DME and higher conversion of methanol were obtained at the reaction temperature of 300° C. and $O_2/MeOH$ ratio of 0.2 as depicted in FIG. 3. FIG. 7 and FIG. 8 depict data from exemplary reaction tests of 3% $Mn/CeO_2$ and 5% $Mn/CeO_2$ catalysts, respectively, at an oxygen/methanol ratio of 0.2. FIG. 9 depicts a comparison of data in FIG. 7 and FIG. 8.

FIG. 10 and FIG. 11 depict data from two stability tests over 80 hours each. These stability tests demonstrated that $Mn/CeO_2$ catalysts don't show any significant deactivation on their methanol conversion and selectivity for DME.

Figure 12:
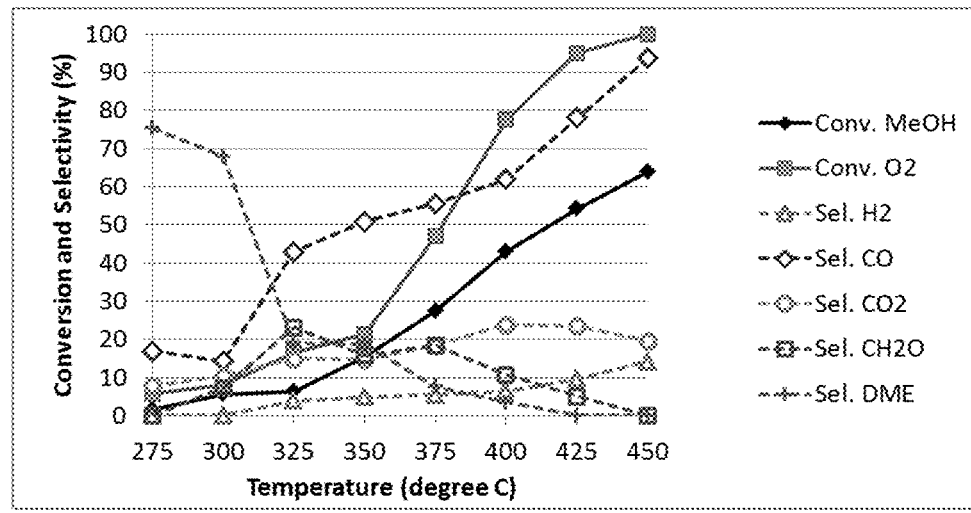
FIG. 12 is a graph depicting methanol and oxygen conversions and selectivity percentiles with respect to hydrogen, carbon monoxide, carbon dioxide, formaldehyde, and dimethyl ether, for reactions in the presence of the cerium oxide catalyst.
Figure 13:
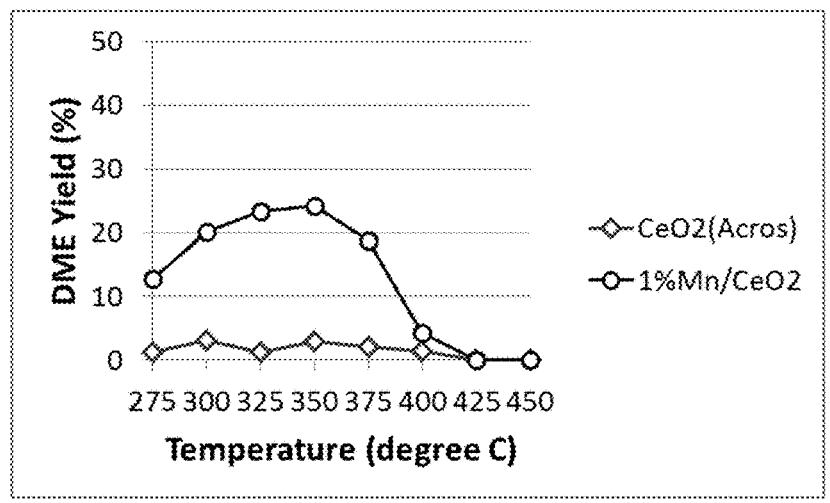
FIG. 13 is a graph depicting a DME yield vs. temperature in the presence of the cerium oxide catalyst and the 1% $Mn/CeO_2$ catalyst.

FIG. 12 and FIG. 13 depict a comparison of a $CeO_2$ support's catalytic efficiency in forming DME as compared to a 1% $Mn/CeO_2$ catalyst's efficiency in forming DME. As shown in FIG. 13, the yield of DME over $CeO_2$ is four to ten times smaller or five to eight times smaller than the yield obtained by using $Mn/CeO_2$ at 300° C. to 375° C. The comparison clarifies that pure $CeO_2$ support does not efficiently catalyze the DME production from methanol. Further, FIG. 14 and FIG. 15 depict data resulting from DME formation with a catalyst comprising only manganese oxide as compared to $Mn/CeO_2$. The data in FIG. 14 and FIG. 15 show that pure manganese oxide does not exhibit any catalytic activity until a temperature of 325° C. When Mn is supported on $CeO_2$, the obtained catalyst produces DME at temperatures as low as 275° C. Taking the data depicted in FIG. 13 and FIG. 15 together, the obtained figures are showing a proof that between Mn and $CeO_2$ arises synergetic effect, that is exploited by the catalyst disclosed in the present invention and the method of producing DME as described herein. The yield of DME over $Mn/CeO_2$ at temperatures of 275° C. to 375° C. is two to five times greater than expected DME yield obtained by sum DME yields of pure $CeO_2$ and manganese oxide, which have no synergetic effect.

DME yields obtained at 300° C. and various $O_2/MeOH$ ratios over $CeO_2$, MnOx and $Mn/CeO_2$ catalysts are organized in Table 4. The results clearly suggest that a synergistic effect between manganese oxide and ceria oxide significantly improves the catalytic activity to produce DME from methanol. The data suggests that $O_2$ improves the production of DME with an $Mn/CeO_2$ catalyst.

TABLE 4

DME yields obtained at 300° C. and various O$_2$/MeOH ratio.

| Sample | O$_2$/MeOH | DME Yield (%) | DME Selectivity (%) |
|---|---|---|---|
| CeO$_2$ | 0.5 | 3.2 | — |
| MnOx | 0.5 | 0.7 | — |
| 1% Mn/CeO$_2$ | 0 | 5.0 | — |
|  | 0.5 | 20.1 | 83 |
|  | 0.3 | 16.8 | 85 |
|  | 0.2 | 19.2 | 86 |
| 3% Mn/CeO$_2$ | 0.2 | 14.4 | 78 |
| 5% Mn/CeO$_2$ | 0.2 | 17.6 | 84 |

Presented herein is a catalyst to produce DME from Methanol with addition of oxygen; a synergistic effect between manganese oxide and cerium oxide has an important role for the reaction; Oxygen with the methanol may efficiently produce DME. The catalyst showed a high stability. 1% Mn/CeO$_2$ and 3% Mn/CeO$_2$ did not show any significant deactivation or decrease of DME selectivity during reaction carried out for longer than 60 h at 300° C. Oxygen may be included in the reactant stream to produce DME.

The invention claimed is:

1. A method of producing dimethyl ether comprising:
   contacting a mixture of methanol and oxygen with a catalyst in a reactor to form the dimethyl ether via oxidative dehydration of methanol,
   wherein the catalyst consists of manganese on a cerium oxide catalyst support, wherein a weight ratio of manganese to the cerium oxide catalyst support is in the range of 0.005 to 0.5.

2. The method of claim 1, wherein the reactor is a fixed bed reactor.

3. The method of claim 1, wherein 1 to 20 mol % of the methanol is converted to dimethyl ether.

4. The method of claim 1, wherein methanol and oxygen are contacted with the catalyst at a temperature in the range of 275° C. to 450° C.

5. The method of claim 1, wherein a selectivity of dimethyl ether from a conversion of 50 to 100 mol % methanol is in the range of 20 to 100%.

6. The method of claim 1, wherein a molar ratio of oxygen to methanol in the mixture of methanol and oxygen is in the range of 0.1:1 to 1:1.

7. The method of claim 1, wherein 20 to 100 mol % of the oxygen is converted to dimethyl ether.

8. The method of claim 1, wherein the catalyst consists of the manganese on a solid porous cerium oxide catalyst support.

9. The method of claim 1, wherein the catalyst does not comprise a zeolite.

10. The method of claim 1, wherein 1 to 50 mol % of the methanol is converted to dimethyl ether.

11. The method of claim 1, wherein the catalyst consists of the manganese as the only active metal on a solid porous cerium oxide catalyst support.

12. The method of claim 1, wherein the catalyst is prepared by
    mixing cerium oxide with a solution comprising manganese salt and a solvent;
    evaporating the solvent to form a solid;
    drying and calcining the solid at a temperature in the range of 100 to 500° C. to form the catalyst, which consists of manganese on a cerium oxide catalyst support, wherein a weight ratio of manganese to the cerium oxide catalyst support is in the range of 0.005 to 0.5.

13. The method of claim 12, further comprising:
    granulating the catalyst to form catalyst grains with a grain size in the range of 0.05 mm to 0.5 mm.

* * * * *